US012773477B2

(12) United States Patent
Seidner H. et al.

(10) Patent No.: US 12,773,477 B2
(45) Date of Patent: Oct. 27, 2026

(54) SCAFFOLDING FOR IMPLANTABLE MEDICAL DEVICES AND METHODS OF USE THEREOF

(71) Applicant: Establishment Labs S.A., La Garita (CR)

(72) Inventors: Ariel Seidner H., La Garita (CR); Nathalia Araujo, La Garita (CR); John Hancock, Santa Barbara, CA (US); Thomas Fuller, La Garita (CR); Arikha Moses, New York, NY (US); Roberto De Mezerville, La Garita (CR); Juan José Chacón Quirós, La Garita (CR)

(73) Assignee: Establishment Labs S.A., La Garita (CR)

( * ) Notice: Subject to any disclaimer, the term of this patent is extended or adjusted under 35 U.S.C. 154(b) by 909 days.

(21) Appl. No.: 17/282,160

(22) PCT Filed: Oct. 3, 2019

(86) PCT No.: PCT/IB2019/058439
§ 371 (c)(1),
(2) Date: Apr. 1, 2021

(87) PCT Pub. No.: WO2020/070694
PCT Pub. Date: Apr. 9, 2020

(65) Prior Publication Data

US 2021/0353831 A1 Nov. 18, 2021

Related U.S. Application Data

(60) Provisional application No. 62/740,518, filed on Oct. 3, 2018.

(51) Int. Cl.
*A61F 2/12* (2006.01)
*A61L 27/18* (2006.01)
(Continued)

(52) U.S. Cl.
CPC ................ *A61L 27/56* (2013.01); *A61F 2/12* (2013.01); *A61L 27/18* (2013.01);
(Continued)

(58) Field of Classification Search
CPC ............. A61F 2/12; A61L 27/60; A61L 27/56
See application file for complete search history.

(56) References Cited

U.S. PATENT DOCUMENTS 4,298,998 A 11/1981 Naficy
5,296,069 A 3/1994 Robert
(Continued)

FOREIGN PATENT DOCUMENTS

BR 112021006348 7/2021
CA 3115057 4/2020
(Continued)

OTHER PUBLICATIONS

Deeken, C. et al., "Mechanical properties of the abdominal wall and biomaterials utilized for hernia repair," *J. Mech. Behavior Biomed. Mater.*, vol. 74, pp. 411-427 (2017).
(Continued)

*Primary Examiner* — Dinah Baria
(74) *Attorney, Agent, or Firm* — SCHWEGMAN LUNDBERG & WOESSNER, P.A.

(57) ABSTRACT

Scaffolding constructs, medical devices comprising scaffolding constructs, and related methods of manufacturing and treatment are described. The scaffolding construct may comprise a biocompatible material, such as a polymer, copolymer, or hydrogel. The scaffolding construct may be porous and at least partially bioresorbable. Further, for example, the scaffolding construct may define a cavity for securing a medical implant therein.

6 Claims, 9 Drawing Sheets

(51) Int. Cl.

| | |
|---|---|
| ***A61L 27/36*** | (2006.01) |
| ***A61L 27/52*** | (2006.01) |
| ***A61L 27/56*** | (2006.01) |
| ***A61L 27/58*** | (2006.01) |
| ***A61L 27/60*** | (2006.01) |
| ***B33Y 80/00*** | (2015.01) |

(52) U.S. Cl.

CPC ........... *A61L 27/3604* (2013.01); *A61L 27/52* (2013.01); *A61L 27/58* (2013.01); *A61L 27/60* (2013.01); *B33Y 80/00* (2014.12); *A61F 2220/005* (2013.01); *A61F 2220/0075* (2013.01); *A61F 2240/001* (2013.01); *A61L 2400/06* (2013.01); *A61L 2430/04* (2013.01)

(56) References Cited

U.S. PATENT DOCUMENTS

| | | | |
|---|---|---|---|
| 6,103,255 A | 8/2000 | Levene et al. | |
| 7,476,249 B2 | 1/2009 | Frank | |
| 8,343,472 B2 | 1/2013 | Adhikari et al. | |
| 8,591,531 B2 | 11/2013 | Buevich et al. | |
| 8,729,202 B2 | 5/2014 | Mayadunne et al. | |
| 8,911,765 B2 | 12/2014 | Moses et al. | |
| 9,023,114 B2 | 5/2015 | Buevich et al. | |
| 9,034,378 B2 | 5/2015 | Moore et al. | |
| 9,080,263 B2 | 7/2015 | Egnelov | |
| 9,382,422 B2 | 7/2016 | Owens et al. | |
| 9,511,171 B2 | 12/2016 | Binette et al. | |
| 9,549,812 B2 | 1/2017 | Shetty et al. | |
| 9,585,744 B2 | 3/2017 | Moses et al. | |
| 9,655,715 B2 | 5/2017 | Limem et al. | |
| D803,401 S | 11/2017 | Limem et al. | |
| 9,888,992 B2 | 2/2018 | Egnelov | |
| 9,888,999 B2 | 2/2018 | Forsell et al. | |
| 10,028,818 B2 | 7/2018 | Fosco et al. | |
| 10,595,986 B2 | 3/2020 | Rehnke | |
| 2007/0276507 A1 | 11/2007 | Bertram et al. | |
| 2009/0216338 A1* | 8/2009 | Gingras | A61F 2/0077 623/23.72 |
| 2010/0152530 A1 | 6/2010 | Timmer et al. | |
| 2010/0256777 A1 | 10/2010 | Datta et al. | |
| 2011/0081397 A1 | 4/2011 | Skalla et al. | |
| 2011/0264213 A1 | 10/2011 | DeMiranda | |
| 2011/0309541 A1 | 12/2011 | Thompson et al. | |
| 2020/0100892 A1* | 4/2020 | Limem | A61L 27/58 |
| 2021/0069374 A1* | 3/2021 | Brennan | B32B 27/40 |

FOREIGN PATENT DOCUMENTS

| | | |
|---|---|---|
| CN | 102083412 | 6/2011 |
| CN | 102470189 | 5/2012 |
| CN | 103491989 | 1/2014 |
| CN | 113015545 | 6/2021 |
| EP | 1537883 | 6/2005 |
| EP | 1537883 A2 | 6/2005 |
| EP | 3860668 | 8/2021 |
| HK | 40059342 | 5/2022 |
| KR | 20210073543 | 6/2021 |
| WO | 2010111458 | 9/2010 |
| WO | WO 2010/111458 A2 | 9/2010 |
| WO | WO 2015/121686 A1 | 8/2015 |
| WO | WO 2017/093528 A1 | 6/2017 |
| WO | WO 2017/196973 A1 | 11/2017 |
| WO | 2020070694 | 4/2020 |

OTHER PUBLICATIONS

International Search Report for PCT/IB2019/058439, dated Dec. 19, 2019 (4 pages).

Kim, John Y. S., and Alexei S. Mlodinow. "What's New in Acellular Dermal Matrix and Soft-Tissue Support for Prosthetic Breast Reconstruction." *Plastic and Reconstructive Surgery,* vol. 140, pp. 30S-43S (2017).

Sforza, M. et al., "Preliminary 3-Year Evaluation of Experience With SilkSurface and VelvetSurface Motiva Silicone Breast Implants: A Single-Center Experience With 5813 Consecutive Breast Augmentation Cases," *Aesthetic Surgery Journal,* vol. 38, pp. 562-573 (2018).

Spear, S.L. et al., "Natrelle Round Silicone Breast Implants: Core Study Results at 10 Years," *Plastic and Reconstructive Surgery,* vol. 133, pp. 1354-1361 (2014).

"Chinese Application Serial No. 201980074670.9, Office Action mailed Jan. 7, 2022", w English translation, 23 pgs.

"International Application Serial No. PCT IB2019 058439, Written Opinion mailed Dec. 19, 2019", 5 pgs.

"International Application Serial No. PCT IB2019 058439, International Preliminary Report on Patentability mailed Apr. 15, 2021", 7 pgs.

"European Application Serial No. 19787455.5, Response to Communication pursuant to Rules 161(1) and 162 EPC filed Nov. 22, 2021", 16 pgs.

"Chinese Application Serial No. 201980074670.9, Response filed Jul. 22, 2022 to Office Action mailed Jan. 7, 2022", w English claims, 15 pgs.

"Chinese Application Serial No. 201980074670.9, Office Action mailed Oct. 27, 2022", w English translation, 20 pgs.

"Brazilian Application Serial No. BR112021006348-0, Office Action mailed Apr. 24, 2023", w/ English translations, 5 pgs.

"Brazilian Application Serial No. BR112021006348-0, Response filed Jul. 26, 2023 to Office Action mailed Apr. 24, 2023", w/ English claims, 22 pgs.

"Chinese Application Serial No. 201980074670.9, Decision of Rejection mailed Mar. 30, 2023", W/ English Claims, 15 pgs.

"Chinese Application Serial No. 201980074670.9, Response filed Dec. 28, 2022 to Office Action mailed Oct. 27, 2022", w/ English claims, 13 pgs.

Guo, Feifei, et al., "The Wisdom of Innovation", w/ English claims, (Jul. 31, 2018), 8 pgs.

Luo, Guofang, et al., "Technical Basis of Metal material detection technology for power grid equipment Fundamentals of Art", w/ English claims, (Nov. 30, 2020), 8 pgs.

"European Application Serial No. 19787455.5, Communication pursuant to Article 94(3) EPC, filed Jun. 12, 2024.", 6 pgs.

* cited by examiner

SCAFFOLDING FOR IMPLANTABLE MEDICAL DEVICES AND METHODS OF USE THEREOF

CROSS-REFERENCE TO RELATED APPLICATIONS

This application is the U.S. national phase entry under 35 U.S.C. § 371 of International Application No. PCT/IB2019/058439, filed on Oct. 3, 2019, which claims priority to U.S. Provisional Application No. 62/740,518, filed on Oct. 3, 2018, which is incorporated by reference herein in its entirety.

TECHNICAL FIELD

The present disclosure relates generally to scaffolding for implantable medical devices, and methods of use thereof.

BACKGROUND

Implantable medical devices may be implanted into patients for a variety of reasons, including, for example, to improve the clinical condition of a patient, to replace natural patient tissue, or for aesthetic purposes. In many cases, implantable medical devices are implanted in patients having severe, complex, or chronic medical conditions. Breast implants are among the largest implantable medical devices in the human body today. For example, breast implants may be used in reconstructive surgeries following mastectomies, e.g., after a cancer diagnosis, surgical removal of breast tissue, radiation therapy, and/or chemotherapy. Due to their volume, mass, and surface area, these implants can present unique physiological interface effects in the surrounding tissues. These effects may include the movement of the implants within the breast pocket after implantation and discomfort to the surrounding tissue. For example, breast implants with a smooth outer surface can slide within the breast pocket and cause discomfort and/or surgical complications for the patient. Moreover, during breast reconstruction procedures, it may be difficult to recreate the proper shape of the breast pocket and to provide sufficient tissue coverage over the implant.

SUMMARY

The present disclosure includes biocompatible scaffolding useful in medical procedures. The scaffolding materials herein optionally may be used with medical implants, including implants used in aesthetic and reconstructive surgeries, and/or may be used in combination with injectable materials, such as filler materials (e.g., hydrogels, hyaluronic acid, fat, etc.). The present disclosure includes devices and compositions comprising materials suitable for such devices, as well as methods of inserting these devices into the human body.

While portions of the following discussion refer to breast implants, the methods and materials disclosed herein may be used in other locations of the body and with other medical implants, such as, e.g., tissue expanders, orthopedic implants, and other implantable medical devices.

The present disclosure includes, for example, a scaffolding construct comprising a biocompatible material; wherein the scaffolding construct is porous and at least partially bioresorbable; and wherein the scaffolding construct defines a cavity for securing a medical implant therein. The scaffolding construct may comprise a polymer or copolymer, such as polyurethane, polyurethane/urea, poly(glycolic acid), poly(lactic acid), poly(lactic-co-glycolic acid), polycaprolactone, or a mixture thereof. Further, for example, the scaffolding construct may be formed from a hydrogel such as, e.g., comprises agarose, alginate, chitosan, collagen, fibrin, gelatin, hyaluronic acid, gelatin methacryloyl, polyethylene glycol, or a mixture thereof. According to some examples herein, the scaffolding construct comprises a secondary material, which may be an injectable material. Exemplary secondary materials include, e.g., fat (heterologous or autologous fat, with respect to a patient receiving the scaffolding construct), a natural filler, a synthetic filler, hyaluronic acid, collagen, or a combination thereof. The secondary material may be disposed within the cavity and/or embedded within pores of the scaffolding construct. According to some aspects herein, the scaffolding construct has an average pore size ranging from about 10 μm to about 200 μm, such as from about 150 μm to about 200 μm. Additionally or alternatively, the scaffolding construct may have a thickness ranging from about 1 mm to about 50 mm. The thickness of the scaffolding construct may be uniform or may vary, e.g., between different areas of the scaffolding construct. In at least one example, the perimeter of the scaffolding construct has a greater thickness than a center portion of the scaffolding construct, e.g., to support sutures or other adhesive or attachment mechanism. The scaffolding construct additionally or alternatively may comprise a bioabsorbable adhesive, sutures, or both, wherein the adhesive and/or sutures attach edges of the scaffolding construct together to form the cavity.

The cavity of the scaffolding constructs herein may have a volume sufficient for completely enclosing an implant, such as a breast implant, or a volume that encloses less than an entirety of an implant, such as a breast implant. The cavity of the scaffolding construct may contain at least a portion of a breast implant, wherein a portion of an outer surface of the breast implant is uncovered by the scaffolding construct. The uncovered outer surface of the breast implant and/or the entire outer surface of the breast implant may have a surface texture, e.g., to promote biocompatibility with surrounding tissues.

The present disclosure further includes methods of treating patients by implanting a scaffolding construct as described above and/or elsewhere herein into a body of the patient. For example, the method may include implanting the scaffolding construct into a body of a patient (e.g., a tissue pocket or other desired target site). The scaffolding construct may have a suitable reabsorption time in the body of the patient. For example, the reabsorption time may range from about 6 months to about 24 months. The scaffolding construct may facilitate formation of a soft tissue capsule at the site of implantation in the body of the patient. Methods of manufacturing the scaffolding constructs herein may include molding or bioprinting the biocompatible material.

The present disclosure further includes a scaffolding construct comprising a biocompatible material; wherein the scaffolding construct is porous and at least partially bioresorbable; wherein the scaffolding construct has an average pore size ranging from about 10 μm to about 200 μm; and wherein the scaffolding construct defines a cavity that includes an implant, an injectable material, or both. The scaffolding construct may comprise, for example, wherein the scaffolding construct comprises polyurethane, polyurethane/urea, poly(glycolic acid), poly(lactic acid), poly(lactic-co-glycolic acid), polycaprolactone, or a mixture thereof. Additionally or alternatively, the scaffolding construct may comprise agarose, alginate, chitosan, collagen, fibrin, gelatin, hyaluronic acid, gelatin methacryloyl, polyethylene glycol, or a mixture thereof. According to some examples herein, the scaffolding construct may be formed from a hydrogel.

According to some aspects, the scaffolding construct may have a thickness ranging from about 1 mm to about 50 mm, which may be uniform or may vary. In some examples, the scaffolding construct comprises an injectable material chosen from fat (e.g., heterologous or autologous fat, relative to a patient to be treated), a natural filler, a synthetic filler, hyaluronic acid, collagen, or a combination thereof. The scaffolding construct may contain an implant, such as a breast implant (e.g., the scaffolding construct and the implant together may be considered to be a medical device). In such cases, at least a portion of an outer surface of the breast implant may be uncovered by the scaffolding construct, wherein the uncovered outer surface of the breast implant has a surface texture.

The present disclosure also includes a medical device comprising an implant and a scaffolding construct at least partially covering an outer surface of the implant. The scaffolding construct may be porous, may be formed from a biocompatible material, and may be at least partially bioresorbable. In some examples, the implant is a breast implant. The biocompatible material may comprise a polymer or copolymer chosen from, e.g., polyurethane, polyurethane/urea, poly(glycolic acid), poly(lactic acid), poly(lactic-co-glycolic acid), polycaprolactone, or a mixture thereof. Additionally or alternatively, the biocompatible material may comprise or be formed from a hydrogel that comprises agarose, alginate, chitosan, collagen, fibrin, gelatin, hyaluronic acid, gelatin methacryloyl, polyethylene glycol, or a mixture thereof. In at least one example, the scaffolding construct defines a cavity that contains the implant, wherein the cavity encloses less than an entirety of the implant. Further, for example, a portion of an outer surface of the implant uncovered by the scaffolding construct may have a surface texture. In some examples, the entire outer surface of the implant has the surface texture. The medical device optionally may comprise a secondary material embedded within pores of the scaffolding construct, the secondary material comprising fat (heterologous or autologous to the patient to be treated), a natural filler, a synthetic filler, hyaluronic acid, collagen, or a combination thereof.

The present disclosure also includes a method of treating a patient, the method comprising implanting a scaffolding construct comprising a biocompatible material into a body of a patient; wherein the scaffolding construct is porous and at least partially bioresorbable; wherein the scaffolding construct defines a cavity that includes an implant, an injectable material, or both; and wherein the scaffolding construct facilitates formation of a soft tissue capsule at a site of implantation in the body of the patient. In some examples, the biocompatible material comprises polyurethane, polyurethane/urea, poly(glycolic acid), poly(lactic acid), poly(lactic-co-glycolic acid), polycaprolactone, agarose, alginate, chitosan, collagen, fibrin, gelatin, hyaluronic acid, gelatin methacryloyl, polyethylene glycol, or a mixture thereof. The scaffolding construct may have a desired reabsorption time in the body of the patient. For example, the reabsorption time may range from about 6 months to about 24 months. The injectable material may comprise fat (heterologous or autologous to the patient to be treated), a natural filler, a synthetic filler, hyaluronic acid, collagen, or a combination thereof. For example, the injectable material may comprise fat that is autologous to the patient. The cavity of the scaffolding construct may contain a breast implant.

The present disclosure also includes a method of manufacturing a scaffolding construct, wherein the method comprises molding or bioprinting a biocompatible material to form a three-dimensional shape of the scaffolding construct, the biocompatible material comprising polyurethane, polyurethane/urea, poly(glycolic acid), poly(lactic acid), poly(lactic-co-glycolic acid), polycaprolactone, agarose, alginate, chitosan, collagen, fibrin, gelatin, hyaluronic acid, gelatin methacryloyl, polyethylene glycol, or a mixture thereof; wherein the scaffolding construct is porous and at least partially bioresorbable; and wherein the scaffolding construct has an average pore size ranging from about 10 μm to about 200 μm and/or a thickness ranging from about 1 mm to about 50 mm. For example, the method may include bioprinting a hydrogel comprising agarose, alginate, chitosan, collagen, fibrin, gelatin, hyaluronic acid, gelatin methacryloyl, polyethylene glycol, or a mixture thereof. In some examples, the method of manufacturing includes attaching edges of the scaffolding construct together to form a cavity and/or adding a secondary material to the scaffolding construct. The secondary material may comprise, for example, fat, a natural filler, a synthetic filler, hyaluronic acid, collagen, or a combination thereof.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various examples and together with the description, serve to explain the principles of the present disclosure. Any features of an embodiment or example described herein (e.g., device, method, etc.) may be combined with any other embodiment or example, and are encompassed by the present disclosure.

DETAILED DESCRIPTION

Figure 1A:
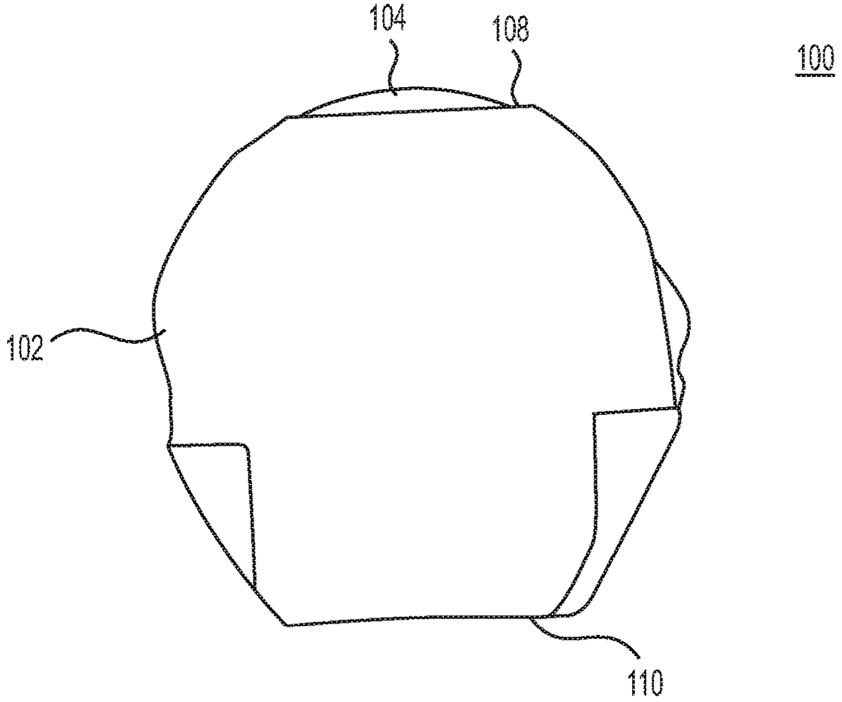
FIGS. 1A and 1B show a top view and a side view of exemplary scaffolding with an implant inserted therein, according to some aspects of the present disclosure.

The terminology herein may be interpreted in its broadest reasonable manner, even though it is being used in conjunction with a detailed description of certain specific examples of the present disclosure. Both the foregoing general description and the following detailed description are exemplary and explanatory only and are not restrictive of the features, as claimed.

In this disclosure, the term "based on" means "based at least in part on." The singular forms "a," "an," and "the" include plural referents unless the context dictates otherwise. The term "exemplary" is used in the sense of "example" rather than "ideal." The terms "comprises," "comprising," "includes," "including," or other variations thereof, are intended to cover a non-exclusive inclusion such that a process, method, or product that comprises a list of elements does not necessarily include only those elements, but may include other elements not expressly listed or inherent to such a process, method, article, or apparatus. The terms "about" and "approximately" are understood to include ±5% of a stated amount or value.

The scaffolding (also referred to herein as scaffolds or scaffolding constructs) disclosed herein may serve to stabilize an implant, e.g., inhibiting or otherwise preventing the movement of an implant relative to surrounding tissues of a patient. Scaffolding materials may allow for improved structuring of a post-operative implantation site, and/or improved positioning and/or anchoring of an implant within the implantation site. Additionally or alternatively, the scaffolding and materials thereof may help promote new tissue growth and/or in reshaping tissue around the implant. For example, in the case of a breast implant, the scaffolding materials herein may assist in reshaping of a breast due to lack of, or insufficient, mammary tissue). The scaffolding materials may be capable of being formed in any desired shape or combination of shapes.

Additionally or alternatively, the scaffolding constructs herein may include one or more secondary materials, which may be injectable. Exemplary secondary materials include, but are not limited to, fat (such as heterologous or autologous fat), natural fillers, synthetic fillers, hyaluronic acid, collagen, and combinations thereof. The secondary material (s) may be any suitable biocompatible material for injecting, implanting, or otherwise supplementing at an implantation site, optionally together with an implant. For example, scaffolding materials with fat grafts may provide for a more natural result at the post-operative implantation site and/or better acceptance (biocompatibility) of scaffolding materials and/or an implant by a patient's body. Further, for example, an injectable material or other secondary material in combination with scaffolding materials may allow for customization, e.g., to accommodate different types, sizes, and shapes of implantation sites.

According to some aspects of the present disclosure, the scaffolding constructs may be configured to at least partially, or completely, cover an implant and/or to enclose, contain, or support a secondary material, such as an injectable material. For example, the scaffolding construct may form a pocket, envelope, or cavity into which an implant (such as a tissue expander or a breast implant, among other types of implantable medical devices) may be inserted, such that a partial outer surface or an entire outer surface of the implant may be covered by the scaffolding material. In a similar fashion, the scaffolding may act as a recipient and/or supporting structure for a secondary material, e.g., an injectable material.

The scaffolding constructs may be configured to at least partially cover, hold (e.g., maintain the position of), and/or stabilize an implant, such as a tissue expander, breast implant, and/or an injectable material such as fat. For example, the scaffolding construct may help to secure the implant within a tissue pocket (e.g., a surgical pocket created before or at the time of surgery). In an exemplary procedure, a scaffolding construct defining a cavity may first be placed into a tissue pocket of the patient's breast tissue. Then, a breast implant may be introduced into the cavity of the scaffolding construct. Optionally, an injectable material or other secondary material may be introduced into the cavity of the scaffolding construct before, after, or during insertion of the breast implant into the cavity.

The scaffolding constructs herein may be used in aesthetic surgeries as well as non-aesthetic surgeries (including, e.g., augmentation procedures, reduction procedures, reconstruction procedures, rehabilitation procedures, etc.). According to a non-limiting exemplary embodiment, the scaffolding constructs herein may prevent or otherwise inhibit movement of a breast implant, tissue expander or filler material (e.g., fat) within a breast pocket.

The scaffolding materials may promote tissue ingrowth from surrounding patient tissues into and through the scaffolding, providing for the formation of a stable "capsule" around the implant, wherein the capsule may be soft and/or supple. For example, the scaffolding may diminish, prevent, or minimize a rigid "capsule" feel of the implant, and thereby improve patient's comfort.

The scaffolding constructs herein may be suitable for use with implants have a surface texture as disclosed in WO 2015/121686, WO 2017/093528, and/or WO 2017/196973, each incorporated by reference herein. For example, the implants may have a combination of surface characteristics (e.g., roughness, kurtosis, skewness, peak height, valley depth, density of contact points, etc.) that provide for improved biocompatibility as compared to implants that lack surface texture or as compared to implants with uncontrolled surface properties. For example, the surface texture of the implants may reduce or eliminate adverse physiological response by patient tissue surrounding the implant. In some examples, the scaffolding may be configured to leave one or more surfaces of the implant exposed, wherein the exposed surface(s) of the implant have a surface texture as disclosed in WO 2015/121686, WO 2017/093528, or WO 2017/196973, each incorporated by reference herein.

In some examples, the implant may have a surface texture, and one or more portions of the implant may be covered by scaffolding while another portion or other portions may be uncovered, such that the surface texture of the implant may be in contact with surrounding tissues of the patient. The scaffolding may help to stabilize the implant by inhibiting or preventing movement of the implant relative to surrounding tissues of the patient after implantation. Additionally or alternatively, when secondary materials are used, the scaffolding may prevent the secondary (e.g., injectable) materials from becoming dispersed and help localize the secondary materials as the intended target site. Thus, for example, the scaffolding materials and scaffolding constructs herein may simultaneously promote tissue growth through the scaffolding material and/or around an implant or secondary/injectable material.

The scaffolding constructs herein may comprise one or more biocompatible, bioreabsorbable materials suitable for implantation in the body. Such material(s) may promote tissue growth and vasculature from surrounding tissue into the scaffolding and around the implant/injectable. Over time, the scaffolding material(s) may be broken down and absorbed by the patient tissue, leaving behind new tissue surrounding the implant or otherwise at a target site. The tissue that is left behind may comprise collagen (e.g., generic collagen growth) and/or may comprise a specific type of tissue guided by the type(s) of material(s) used for the scaffolding and/or secondary materials used with the scaffolding. Such tissue may help to maintain a proper position of the implant and/or secondary material(s) (e.g., injectable material(s)), stabilize the implant within the patient after the scaffolding material has been absorbed and generate volumes of viable tissue.

The scaffolding disclosed herein may comprise a bioreabsorbable material or combination of bioreabsorbable materials. Exemplary scaffolding materials may include, but are not limited to, biodegradable polymers and copolymers, such as polyurethane, polyurethane/urea, poly(glycolic acid), poly(lactic acid), poly(lactic-co-glycolic acid), polycaprolactone, and mixtures thereof. In some examples, the scaffolding material may comprise a thermoset material, such as polyurethane/urea copolymer. Further, for example, the scaffolding may comprise or be formed from a hydrogel, including, e.g., hydrogels based on agarose, alginate, chitosan, collagen, fibrin, gelatin, hyaluronic acid, gelatin methacryloyl (GelMa), poly(ethylene glycol), Matrigel™, Pluronic® F-127, and any combinations thereof.

The hydrogels or other biocompatible materials used in the scaffolding constructs herein optionally may be embedded with one or more growth factors (such as, e.g., vascular endothelial growth factor (VEGF), fibroblast growth factor (FGF), and/or epidermal growth factor (EGF), among other types of growth factors), peptides (such as, e.g., arginylglycylaspartic acid (RGD)) and cells (such as, e.g., Mesenchymal Stem Cells) and any combinations thereof. Furthermore, the scaffolding may be built with a combination of synthetic polymers and hydrogels.

According to some aspects of the present disclosure, the scaffolding may be removed during the implantation procedure and/or after the implantation procedure. For instance, the scaffolding material may comprise one or more magnetic materials, wherein magnetic force may be used to remove the scaffolding material during and/or after the implantation procedure.

According to a non-limiting exemplary embodiment, the scaffolding may comprise a bioreabsorbable polyurethane polymer or polyurethane/urea copolymer. The polymer or copolymer may be porous (e.g., prepared by foaming a polymer or polymer mixture so as to form a porous construct or by altering the aperture width and pitch of the weave in the case of using threads of synthetic polymer) to provide a scaffolding having interstices through which tissue and vasculature may form after implantation of the scaffolding in the body.

In some examples, the types of scaffolding materials, the thickness of the scaffolding, and/or the pore size of the scaffolding may provide for a reabsorption time ranging from about 6 months to about 24 months, e.g., from about 12 months to about 18 months, from about 6 months to about 12 months, from about 12 months to about 24 months, or from about 18 months to about 24 months after implantation. This time period may allow new tissue and vasculature to have formed around the implant to help in maintaining proper positioning of the implant.

According to some aspects of the present disclosure, sutures (e.g., bioresorbable sutures) may be used to assist in holding the scaffolding construct in appropriate position relative to the implant during implantation. The scaffolding construct may maintain the appropriate position by friction force between the scaffolding material and the implant. Further, sutures (e.g., bioresorbable sutures) may be used to attach the scaffolding to surrounding tissue to maintain the position of the scaffolding construct and the implant relative to the surrounding tissue. Additionally or alternatively, friction force between the scaffolding and the surrounding tissue may serve to maintain the position of the scaffolding construct and the implant relative to the surrounding tissue.

The thickness of the scaffolding may affect the amount of time for the scaffolding material to be reabsorbed. Scaffolding having a greater thickness may generally provide a stronger construct to manipulate and support the implant. Moreover, thicker scaffolding may provide for thicker tissue formation, the tissue being soft and vascularized. The thickness of the scaffolding materials may be selected to achieve the desired reabsorption time and/or provide the desired support around the implant.

The thickness of the scaffolding may be uniform, or the scaffolding may have one or more portions or regions having a thickness greater or less than one or more other portions or regions of the scaffolding. In some examples, the thickness of the scaffolding may range from about 1 mm to about 90 mm, such as from about 5 mm to about 50 mm, from about 3 mm to about 8 mm, from about 10 mm to about 20 mm, from about 50 mm to about 75 mm, from about 25 mm to about 35 mm, from about 15 mm to about 30 mm, or from about 18 mm to about 32 mm. For example, the thickness may be between about 1 mm and about 10 mm, e.g., between about 2 mm and about 5 mm, or between about 2 mm and about 4 mm. In some embodiments, the thickness of the scaffolding construct may be uniform and have a thickness of at least about 1 mm, 2 mm, 3 mm, 4 mm, or more. Further, for example, the uniform thickness of the scaffolding construct may be at most about 4 mm, 3 mm, 2 mm, 1 mm, or less.

As mentioned above, in some instances, the thickness of the scaffolding may vary, depending on considerations such as the configuration of the scaffolding, the amount and/or type of patient tissue to support, the shape of the implant, the size of the implant, and/or the type of implant. For example, one or more portions of the scaffolding may have a greater thickness to provide more support around certain areas of the implant. In the case of a breast implant, for example, a scaffolding construct may have a greater thickness below the implant, e.g., to better support the weight of tissue and/or the implant due to gravity when a patient is standing. Additionally or alternatively, one or more portions of the scaffolding may have a greater thickness to facilitate suturing portions of the scaffolding together, to the implant, and/or to surrounding tissues. For example, the perimeter of the scaffolding construct may have a greater thickness than other portions of the scaffolding in order to accept and support sutures at or proximate the perimeter of the scaffolding. Further, for example, multiple pieces of scaffolding may be sutured together to form various shapes, and the areas of the scaffolding that are intended to be joined may be thicker to provide additional support for sutures. In some examples, the maximum thickness of the scaffolding may be 4 mm or less, such as from about 1 mm to 4 mm, or from about 2 mm to about 3 mm. In at least one example, the scaffolding may be formed in a three-dimensional (3D) shape and have a uniform thickness.

Additionally or alternatively to having the exemplary thicknesses above, the scaffolding may have an average pore size ranging from about 150 μm to about 200 μm, e.g., about 170 μm. Thus, for example, the average pore size may be at least 10 μm, 20 μm, 30 μm, 40 μm, 50 μm, 100 μm, 110 μm, 120 μm, 130 μm, 140 μm, 150 μm, or more and/or at most 200 μm, 180 μm, 160 μm, 150 μm, 100 μm, 90 μm, 80 μm, 70 μm, 60 μm, or less. In some examples, the average pore size of the scaffolding may range from about 10 μm to about 200 μm, from about 20 μm to about 50 μm, from about 10 μm to about 30 μm, from about 75 μm to about 125 μm, from about 120 μm to about 150 μm, from about 80 μm to about 110 μm, or from about 40 μm to about 90 μm.

The scaffolding may be configured to cover at least a portion, or all, of an implant. According to a non-limiting example, the geometry/shape of the scaffolding construct may form an envelope (e.g., a pocket or sleeve) configured to receive a generally round, oval, or teardrop shaped implant (e.g., breast implant or tissue expander), optionally along with a secondary material, e.g., an injectable material such as fat.

As described above, the shape of the scaffolding construct may be defined by attaching different portions (e.g., two or more edges) of a piece of scaffolding material together and/or by attaching multiple pieces of scaffolding material together to form the construct. While certain scaffolding constructs may be configured to completely surround (e.g., encapsulate) an implant, such as a breast implant, the scaffolding may be in any shape suitable to assist in stabilizing and/or maintaining the position of an implant or part of an implant. The shape of the scaffolding may be any other shape suitable for receiving an implant. In some embodiments, the scaffolding may have the same or a similar shape as the implant. Further, for example, the scaffolding may include asymmetrical sleeves and/or discrete patches of scaffolding material(s) intended to cover distinct areas of the implant while leaving other areas exposed. This type of configuration may be useful to allow the scaffolding materials to elicit a targeted growth of tissue in identified areas or regions of the implant, e.g., to assist in stabilization. Additionally or alternatively to scaffolding designed to cover distinct areas of an implant, the scaffolding size may also be adjusted to allow for areas where a secondary material (e.g., an injectable material) could be placed alongside an implant.

Figure 1B:
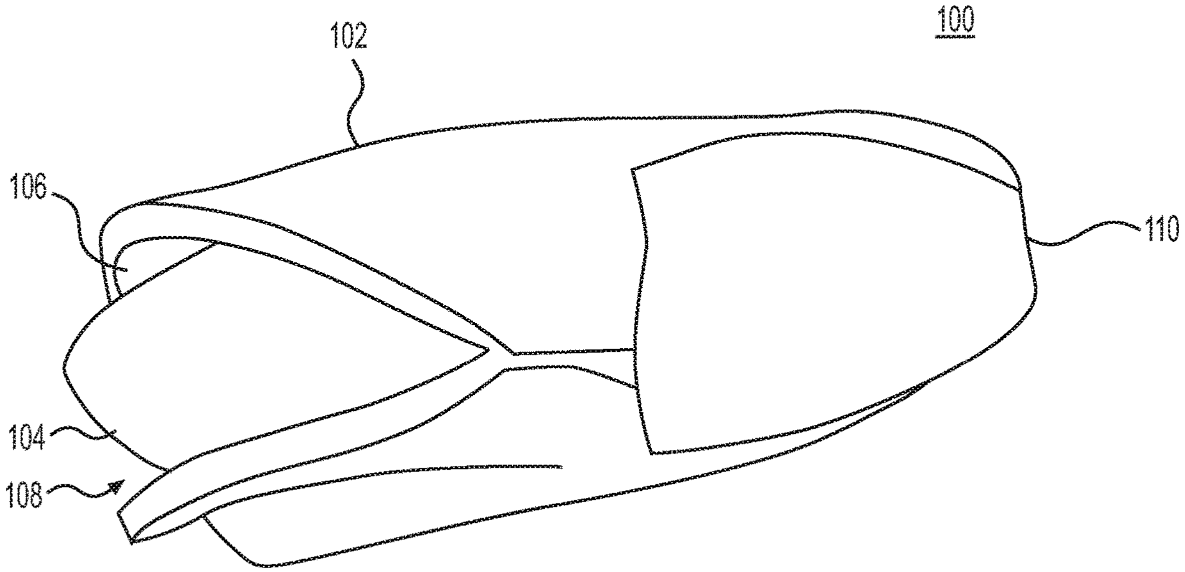

FIGS. 1A and 1B depict an exemplary scaffolding construct 102 according to some aspects of the present disclosure. As shown, the scaffolding construct 102 defines a cavity with an implant 104, e.g., a breast implant, disposed within the cavity. For example, the implant 104 may be a breast implant that has a round, oval, or teardrop shape. The scaffolding construct 102 as shown includes an open end 108 and a closed end 110, and has a generally circular shape. The scaffolding construct 102 may act as a sleeve or an envelope covering the majority of the implant 104. Optionally, an injectable material, e.g., a filler material such as fat, may be introduced into the cavity, e.g., between the implant 104 and the scaffolding construct 102, and/or the injectable material may be incorporated into the scaffolding material.

Figure 2:
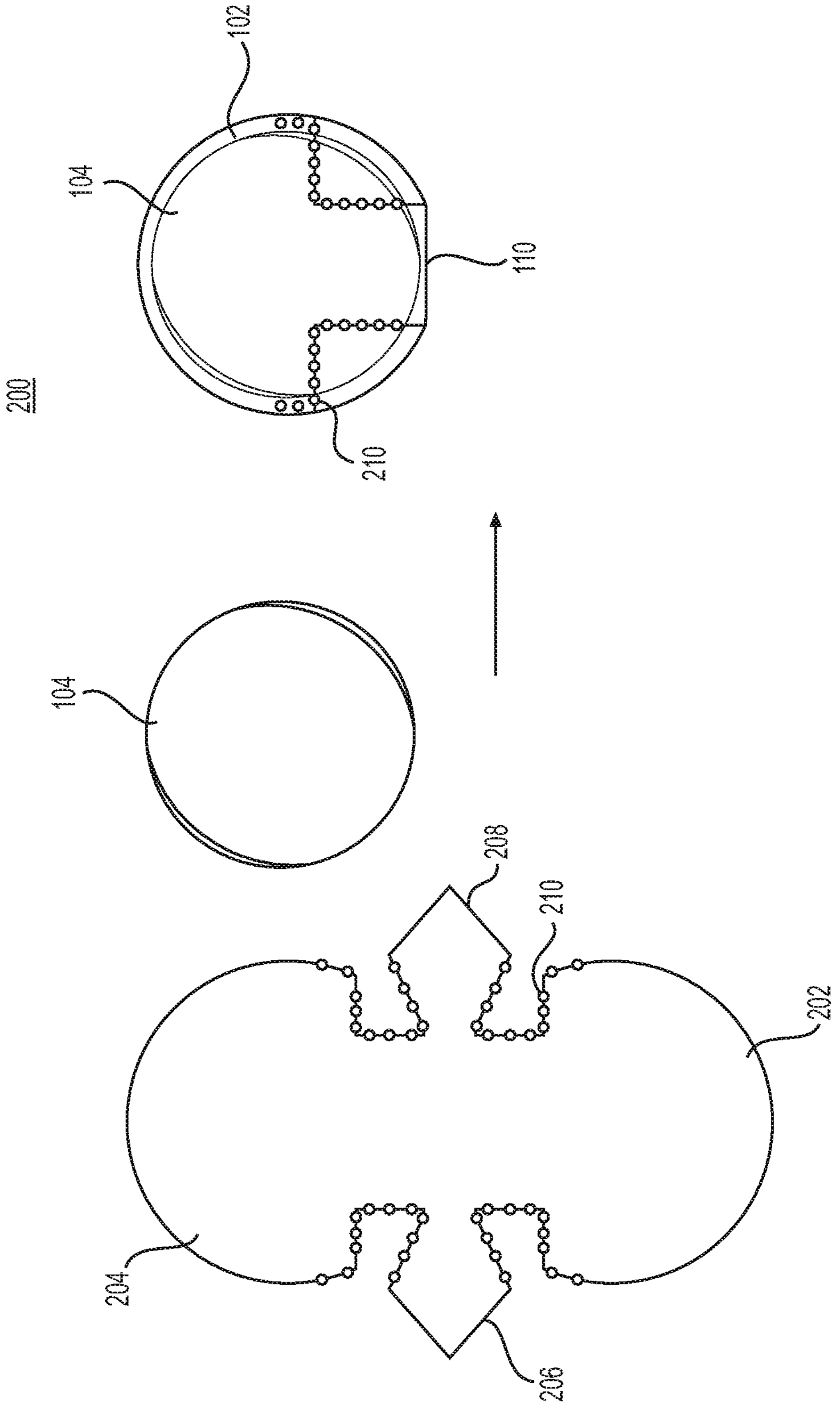
FIGS. 2-7 show exemplary scaffolding, according to some aspects of the present disclosure.

FIG. 2 illustrates a piece of scaffolding material 200 that may be assembled into the scaffolding construct 102 depicted in FIGS. 1A-1B. The piece of scaffolding material 200 may have two semi-circular regions 202, 204 and two side portions 206, 208. Markings 210 indicate areas of attachment, e.g., via biocompatible/biodegradable adhesive, biodegradable sutures, or other attachment mechanism, such that the edge of one portion of the piece of scaffolding material 200 is joined to the edge of another portion of the piece of scaffolding material 200. Folding the piece of scaffolding material 200 and assembling along the markings 210 may produce the scaffolding construct 102 depicted in FIGS. 1A-1B. The piece of scaffolding material 200 may form a continuous thickness of scaffolding 102 for surrounding the implant 104. The configuration illustrated in FIG. 2 may provide additional support for the implant and allow for a secure fit of the implant within the scaffolding construct, e.g., avoiding gaps forming between the scaffolding construct and the implant surface.

Figure 3:
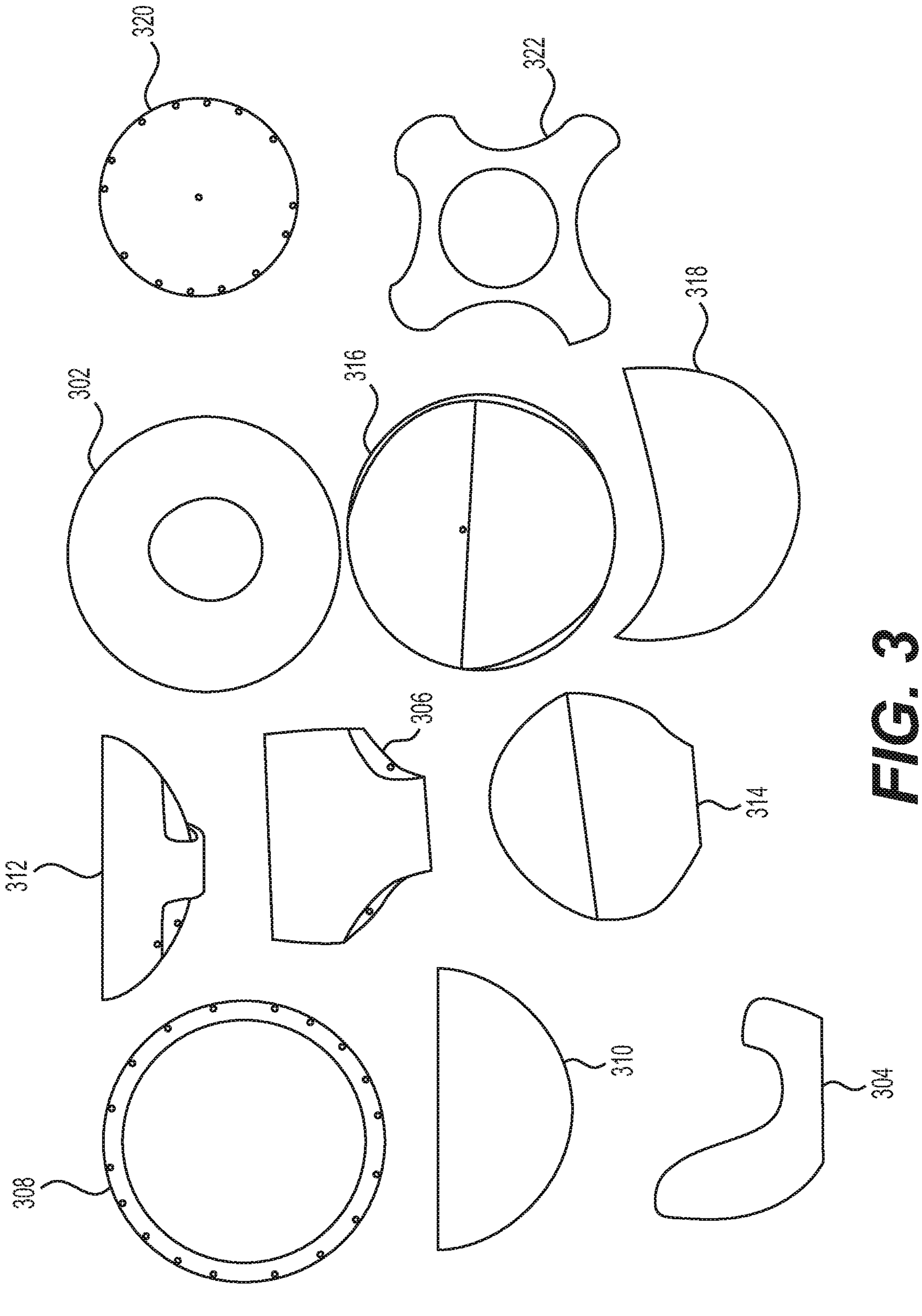

FIG. 3 depicts additional exemplary scaffolding constructs with different shapes. Any of the constructs illustrated may be used in combination with an implant having a surface texture as discussed above. For instance, the scaffolding construct 302 has an annular shape with an aperture. This shape may provide support to an implant around the periphery of the implant while exposing the central portions of the front and back of the implant (thus allowing the implant to contact surrounding tissue). Scaffolding construct 304 has an asymmetrical shape, e.g., that may provide support to an implant and allow a greater surface area of the implant to be exposed to surrounding tissue when implanted. Scaffolding construct 306 has a more symmetrical shape and may provide support to an implant while allowing a greater surface area of the implant to be in contact with the surrounding tissue.

Further referring to FIG. 3, scaffolding construct 308 is generally annular in shape, thinner than construct 302, wherein scaffolding construct 308 has sutures around the circumference to enclose an implant. Scaffolding construct 310 has a semi-circular shape, e.g., to allow half of a rounded implant to be exposed to the surrounding tissue when implanted. Scaffolding construct 312 may provide support similar to the scaffolding construct 306, while allowing a greater surface area of the implant to be exposed to the surrounding tissue when implanted. Scaffolding construct 314 has a generally circular shape on one side and a semi-circular shape on the other side to provide full support to one side of the implant and expose half of the other side of the implant to the surrounding tissue when implanted. Scaffolding construct 316 may provide support to the implant while fixing the implant via sutures in the center and exposing at least part of the periphery of the implant to the surrounding tissue when implanted. Scaffolding construct 318 may provide support in a manner similar to the scaffolding construct 310 while allowing a smaller surface area of the implant to be exposed to the surrounding tissue when implanted. Scaffolding construct 320, similar to scaffolding construct 308, may be in a circular shape with sutures around the circumference and at or proximate the center so that implant may be completely enclosed and fixed in the scaffolding construct 320. Scaffolding construct 322 may provide support to the implant around the periphery of the implant while exposing at least part of the periphery of the implant and the front and back of the implant to the surrounding tissue when implanted.

As previously discussed, attachment mechanism (e.g., adhesive, sutures, etc.) may be used to maintain the position of the scaffolding relative to the implant during implantation. In the following examples (illustrated in FIGS. 4-6), a biocompatible adhesive may be used, and/or sutures or other attachment mechanisms may be used. In some examples, ultrasonic welding or heat welding, e.g., with a suitable adhesive, may be used to form the scaffolding constructs.

Figure 4:
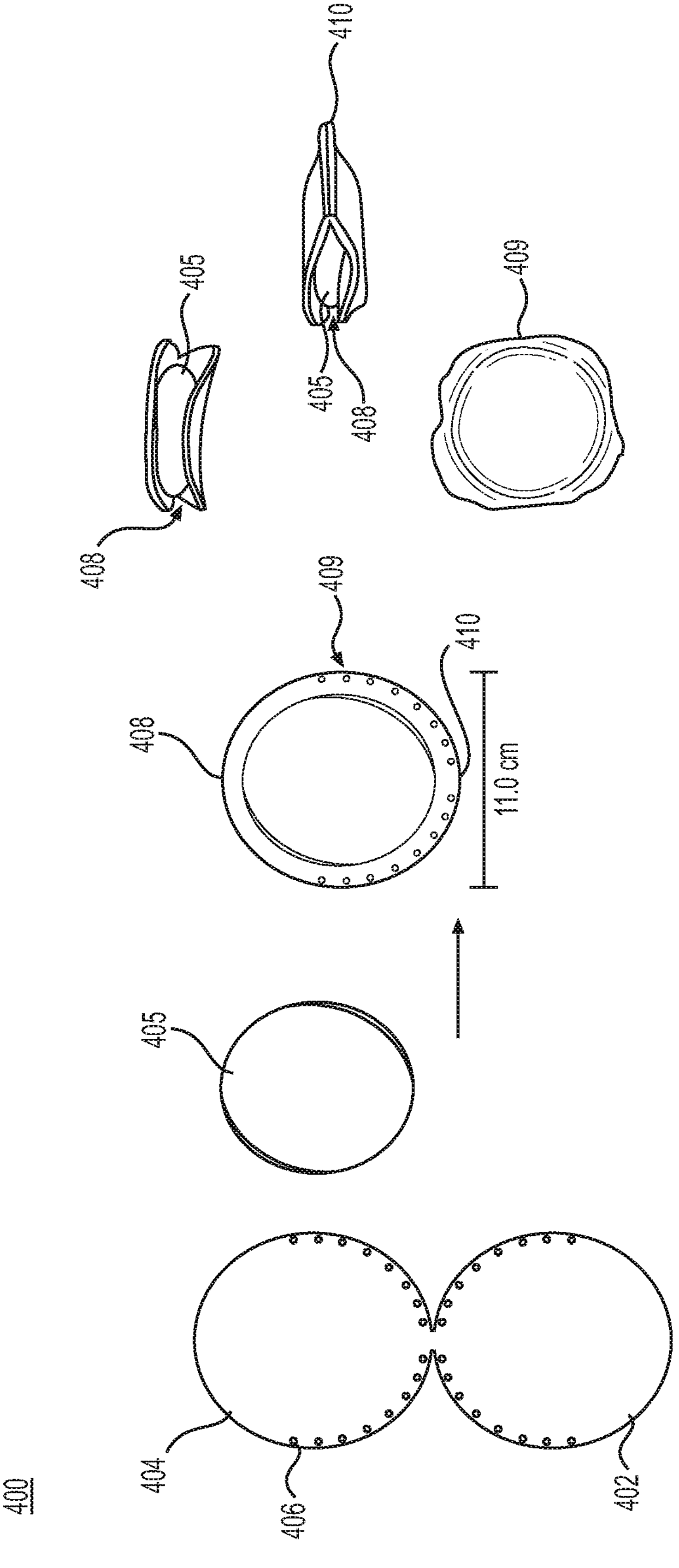

FIG. 4 illustrates an exemplary scaffolding construct 409 suitable for enclosing an entire implant 405, e.g., using a biocompatible adhesive and/or sutures indicated by markings around the perimeter of a piece of scaffolding material 400 used to assemble construct 409. The piece of scaffolding material 400 has an end-to-end envelope shape with two rounded or circular portions 402, 404. A plurality of markings 406 indicate areas of suture or other attachment mechanism (e.g., biocompatible/biodegradable adhesive), such that the edge of one portion 402 of the piece of scaffolding material 400 is joined to the edge of another portion 404 of the piece of scaffolding material 400. After folding the piece of scaffolding material 400 to assemble the construct 409, the scaffolding construct 409 may be generally circular shape, with an open end 408 and a closed end 410. As shown in FIG. 4, the diameter of the circular shape may be about 11 cm in at least one example, although this is non-limiting and other dimensions are encompassed herein. The implant 405 may be disposed within a cavity formed by the scaffolding 409.

Figure 5:
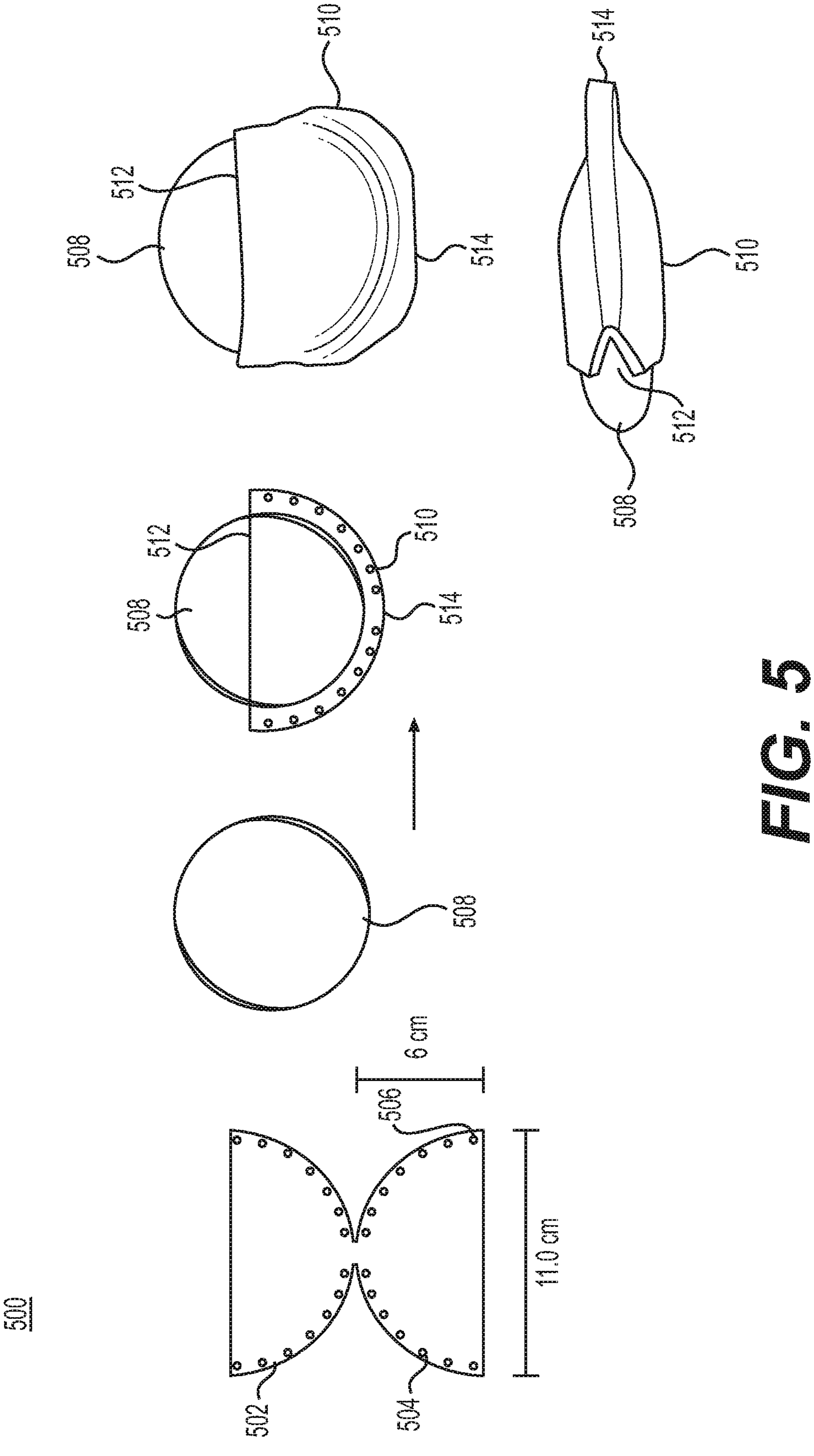

FIG. 5 illustrates another non-limiting example for forming a scaffolding construct suitable for receiving portions of an implant, e.g., using a biocompatible adhesive (indicated by markings around the perimeter). The piece of scaffolding material (with an end-to-end envelope shape) 500 may include two rounded, e.g., semi-circular, portions 502, 504. One or more markings 506 may indicate areas of suture/attachment via a biocompatible and/or bioresorbable adhesive, such that the edge of one portion of the piece of scaffolding material 500 is joined to the edge of another portion of the piece of scaffolding material 500. As shown in FIG. 5, the one or more markings 506 may only cover partial circumstance of each of the rounded portions 502, 504. After folding the piece of scaffolding material 500 and suturing the markings 506, the scaffolding construct 510 may be in a semi-circular shape, with an open end 512 and a closed end 514. As shown in FIG. 5, an exemplary diameter of the semi-circular shape may be 11 cm, however this is non-limiting and other sizes are contemplated herein. The implant 508 may be disposed within the cavity formed by the scaffolding construct 510.

Figure 6:
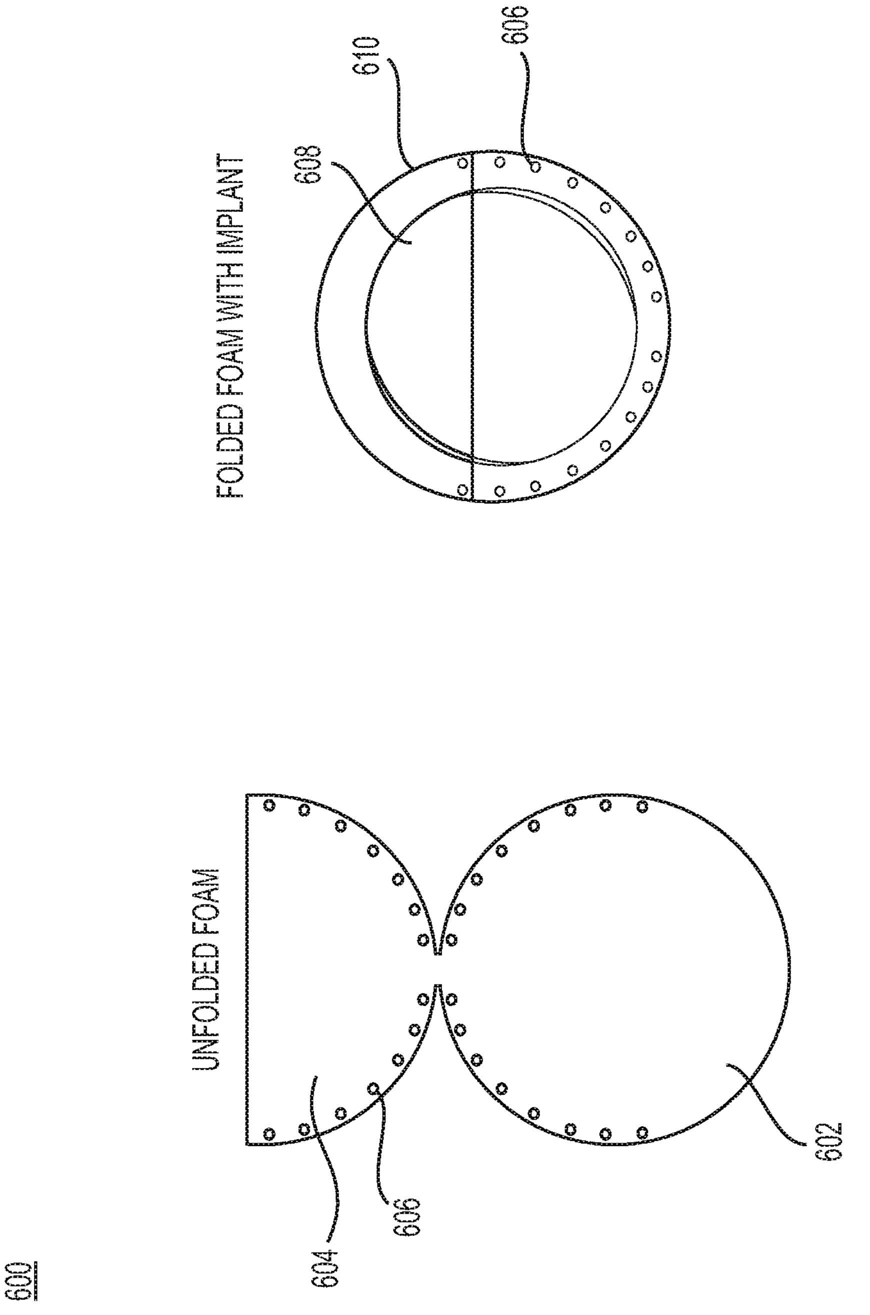

FIG. 6 illustrates asymmetric scaffolding suitable for receiving portions of an implant, e.g., using a biocompatible adhesive (indicated by markings around the perimeter). The piece of scaffolding material (with an end-to-end envelope shape) 600 may include rounded portions 602, 604. One or more markings 606 may indicate areas of suture/attachment via biocompatible/bioresorbable adhesive, such that the edge of one portion of the piece of scaffolding material 600 is joined to the edge of another portion of the piece of scaffolding material 600. As shown in FIG. 6, one or more markings 606 may cover the peripheral of the portion 604 and half of the periphery of the portion 602. After folding the piece of scaffolding material 600 and suturing the one or more markings 606, the scaffolding construct 610 may be in a generally circular shape, with one side fully covering the implant 608 and the other side exposing approximately half of the implant 608. The implant 608 may be disposed within the cavity formed by the scaffolding construct 610.

The scaffolding constructs illustrated in FIG. 5 and/or FIG. 6 may be beneficial for use in conjunction with a texturized breast implant, wherein the scaffolding may provide direct support to areas of breast tissue subject to the greatest weight of the implant (e.g., while a patient is standing) while simultaneously allowing the implant to have greater contact with surrounding tissue. The texturized breast implant may have a surface texture as disclosed in WO 2015/121686, WO 2017/093528, or WO 2017/196973, incorporated by reference herein.

Figure 7:
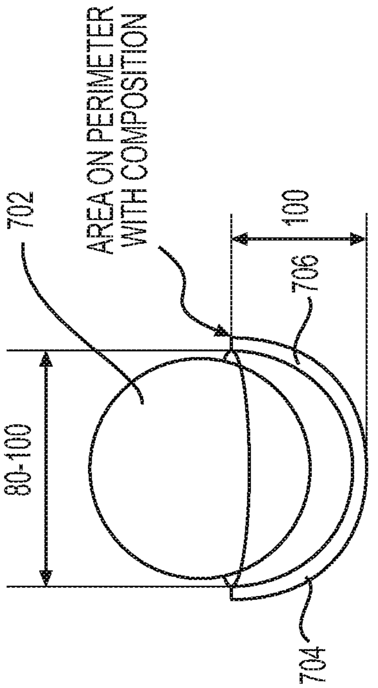

FIG. 7 shows exemplary scaffolding having a shape corresponding to an exemplary breast implant or tissue expander. As shown in FIG. 7, the implant 702 may be placed in a cavity of the scaffolding construct 704 prior to implantation. The implant 702 may have a generally round shape, e.g., having a diameter ranging from about 8 cm to about 10 cm. The scaffolding construct 704 may have a generally semi-circular shape with a radius of about 10 cm. Optionally, the scaffolding construct 704 may have one or more target areas 706 (e.g., the peripheral of the scaffolding) having increased mechanical strength. The scaffolding construct 704 may house both an implant 702 and a desired amount of a secondary material, such as an injectable material. During a surgical procedure, the scaffolding construct 704 containing the implant (optionally together with an injectable material) may be implanted, optionally with the use of an insertion tool such as an insertion sleeve, into a tissue pocket of a patient. The scaffolding construct 704 may be placed at any suitable positions and orientation in breast tissue, including, e.g., the lower part of the breast, the upper part of the breast, or the middle part of the breast. The implant may have a surface texture as disclosed in WO 2015/121686, WO 2017/093528, or WO 2017/196973, incorporated by reference herein.

According to some aspects of the present disclosure, the scaffolding construct or material(s) thereof may include additional or alternative support structures (e.g., a biodegradable film and/or foam). For example, the scaffolding may comprise a biodegradable film between two pieces of porous scaffolding material (see FIG. 8A). Additionally or alternatively, the scaffolding construct may include a film at least partially covering a surface of the scaffolding material (e.g., an outer or inner surface of the scaffold). The film(s) may provide a reinforced structure to the scaffolding construct to increase support, integrity, and/or mechanical strength, e.g., to allow the scaffolding material to accept sutures without tearing, while also allowing tissue ingrowth and reabsorption, as discussed above. The film may be biodegradable and may comprise the same or a similar bioreabsorbable material (e.g., poly(L-lactic acid) or poly (p-dioxanone)) as the porous (e.g., foamed) portion(s) of the scaffolding. Thus, for example, the added support provided by the film may allow for tissue and vascularity ingrowth into the porous scaffolding and around the implant.

Figure 8A:
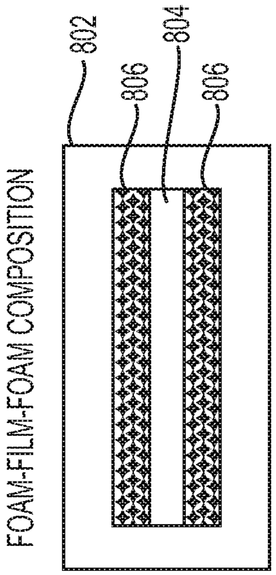
FIGS. 8A-8B show schematics for exemplary compositions of scaffolding materials, according to some aspects of the present disclosure.
Figure 8B:
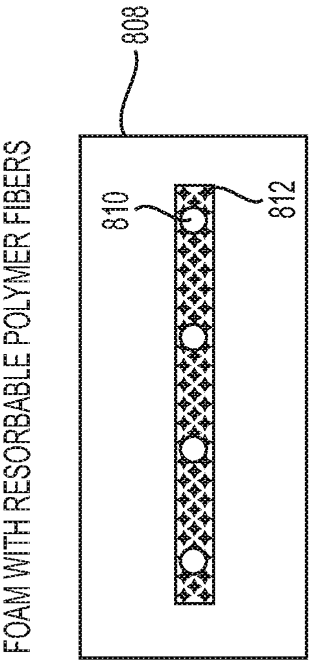

FIGS. 8A-8B depict exemplary additional or alternative support structures that may be incorporated into the scaffolding constructs herein. For example, FIG. 8A shows a partial cross-section view of scaffolding construct including a biodegradable film. As shown in FIG. 8A, the scaffolding construct 802 may include a film 804 disposed within the porous scaffolding materials 806. This film 804 may be bioresorbable and may comprise the same or a similar material(s) as the scaffolding materials 806, e.g., a bioresorbable polymer or copolymer, or a hydrogel. FIG. 8B shows a partial cross-section view of scaffolding with bioreabsorbable fibers. As shown in FIG. 8B, the scaffolding 808 may include one or more fibers 810 placed in the porous scaffolding materials 812. The porous scaffolding material 812 may include one or more fibers 810 embedded therein, e.g., to form a weave or a grid of fibers to reinforce the porous scaffolding materials 812. These fibers 810 may be bioresorbable and may comprise the same or a similar material as the porous scaffolding materials and/or film 804, e.g., a bioresorbable polymer or copolymer. Additionally, as illustrated in FIG. 7, the scaffolding may have target areas 706 having increased mechanical strength. The fibers 810 may be provided throughout the entire porous scaffolding materials 812 of the scaffolding 808 (including, e.g., scaffolding having a foam-film-foam configuration as described above), or the fibers 810 may be provided in one or more targeted areas or regions 706 of the porous scaffolding materials to add mechanical strength, as shown in FIG. 7.

In some examples, the scaffolding may be soft, elastic, and pliable so as to fit snugly over the implant, e.g., to inhibit relative movement between the scaffold and the implant. Accordingly, when the scaffolding and implant are implanted in the patient, the scaffolding may help to maintain a proper position of the implant in the desired area (e.g., breast implant within a breast pocket).

The scaffolding may be form via different manufacturing processes, including casting (e.g., die casting), coating (e.g., laser engraving), molding (e.g. injection molding), forming (e.g., shearing), machining (e.g., mills), joining (e.g., welding), or additive manufacturing (e.g., 3D printing). According to a non-limiting exemplary embodiment, the scaffolding may comprise a bioreabsorbable hydrogel formulation. The hydrogel may be assembled into a desired shape using 3D bioprinting technologies and methods. The hydrogel material can be printed in a simple slab/sheet format that can then be used in a similar fashion as traditional acellular dermal matrices (with thickness ranging from 100 μm to 6 cm). The hydrogel material can also be built into complex shapes using the FRESH (Freeform reversible embedding of suspended hydrogels) method. In this situation, the hydrogel scaffolding formed with hydrogel material can have features with a resolution of about 200 μm, with gradients in pore sizes, thickness and materials. Furthermore, the hydrogel scaffolding may vary in resorption time which can be tuned from a couple of hours to about 20 days by modifying the crosslink density of the hydrogel materials. The hydrogel scaffolding may be reinforced with synthetic polymers as well. The synthetic polymers may include inorganic polymers (e.g., polysiloxane), or organic polymers (e.g., low-density polyethylene, polystyrene).

Figure 9B:
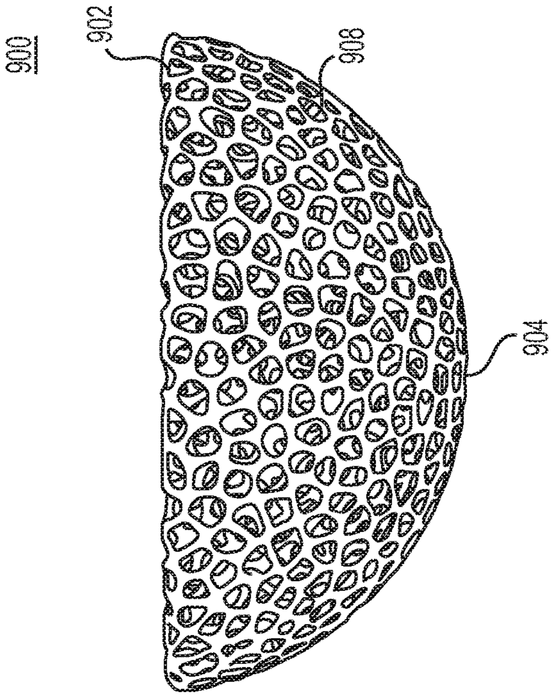
FIGS. 9A-9C show an exemplary scaffolding formed via 3D bioprinting, according to some aspects of the present disclosure.
Figure 9A:
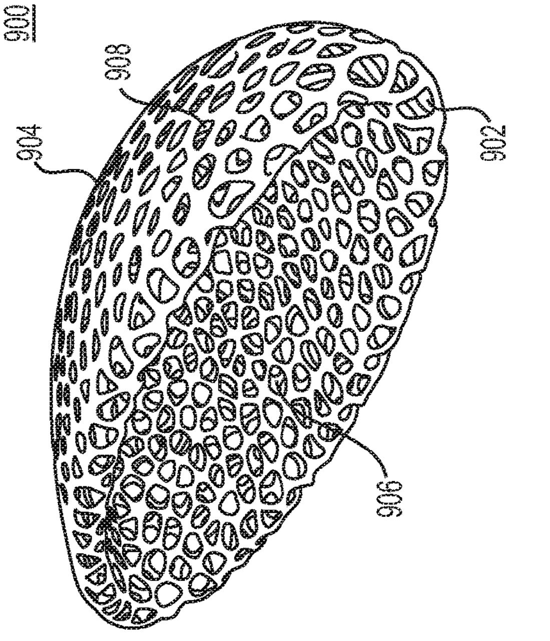
Figure 9C:
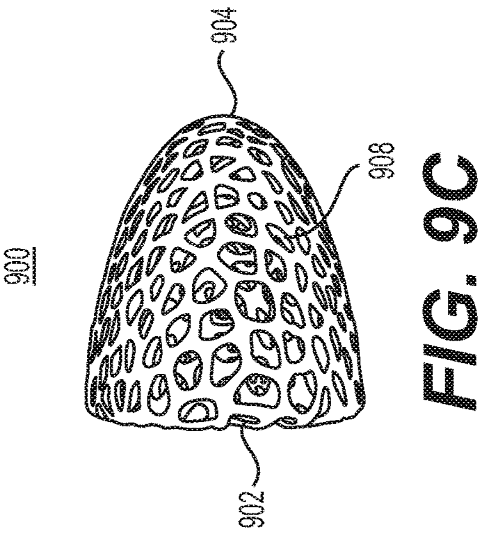

FIGS. 9A-9C depict a perspective view, a top view, and a side view of an exemplary hydrogel scaffolding. As shown in FIGS. 9A-10C, the hydrogel scaffolding 900 may include an open end 902 and a closed end 904. In the top view of FIG. 9B, the hydrogel scaffolding 900 may be in a generally semi-circular shape. The hydrogel scaffolding 900 may act as sleeve covering an implant. The implant may be disposed within the cavity 906 formed by the hydrogel scaffolding 900. The hydrogel scaffolding 900 may include one or more pores 908 allowing a greater surface area of the implant to be exposed to the surrounding tissue when implanted. In some embodiments, an injectable such as fat may be added with the implant or replace the space where the implant is in the cavity 906 of the hydrogel scaffolding 900. The thickness of the hydrogel scaffolding may vary depending on the size of the implant. In some embodiments, thicker hydrogel scaffolding may be used so the size of the implant, which is not resorbable, can be reduced.

The hydrogel scaffolding, as described above, may be manufactured via 3D bioprinting. The 3D bioprinting may refer to sequential addition of biomaterial layer or joining of biomaterial layers (or parts of biomaterial layers) to form a 3D structure, in a controlled manner. The controlled manner may include automated control. In the 3D bioprinting process, the deposited biomaterial can be transformed to subsequently harden and form at least a part of the 3D object. 3D bioprinting may include layered manufacturing. The biomaterial (or bioink) used for the 3D bioprinting may include natural and synthetic structural proteins, such as fibrinogen, albumin, fibronectin, collagen, decellularized ECMs, or hyaluronic acid; polymers, such as pluronic or urethanes; living biological components, such as undifferentiated stem cells, partially differentiated stem cells, terminally differentiated cells, microvascular fragments, or organelles; macromolecules; and/or pharmaceuticals.

The scaffolding and scaffolding materials thereof disclosed herein may provide one or more of the following effects or benefits: 1) promote implant/injectable stability in combination with biocompatibility, 2) promote healthy tissue growth through the construct and around implants/injectable for patients, e.g., including patients that have a thin or relatively thin dermal layer, 3) promote formation of specific types of tissue around the implant, such as adipose tissue, and/or 4) reduce the cost of scaffolding.

The following examples are intended to illustrate the present disclosure without, however, being limiting in nature. It is understood that the present disclosure encompasses additional embodiments consistent with the foregoing description and following examples.

EXAMPLES

Example 1

Figure 10:
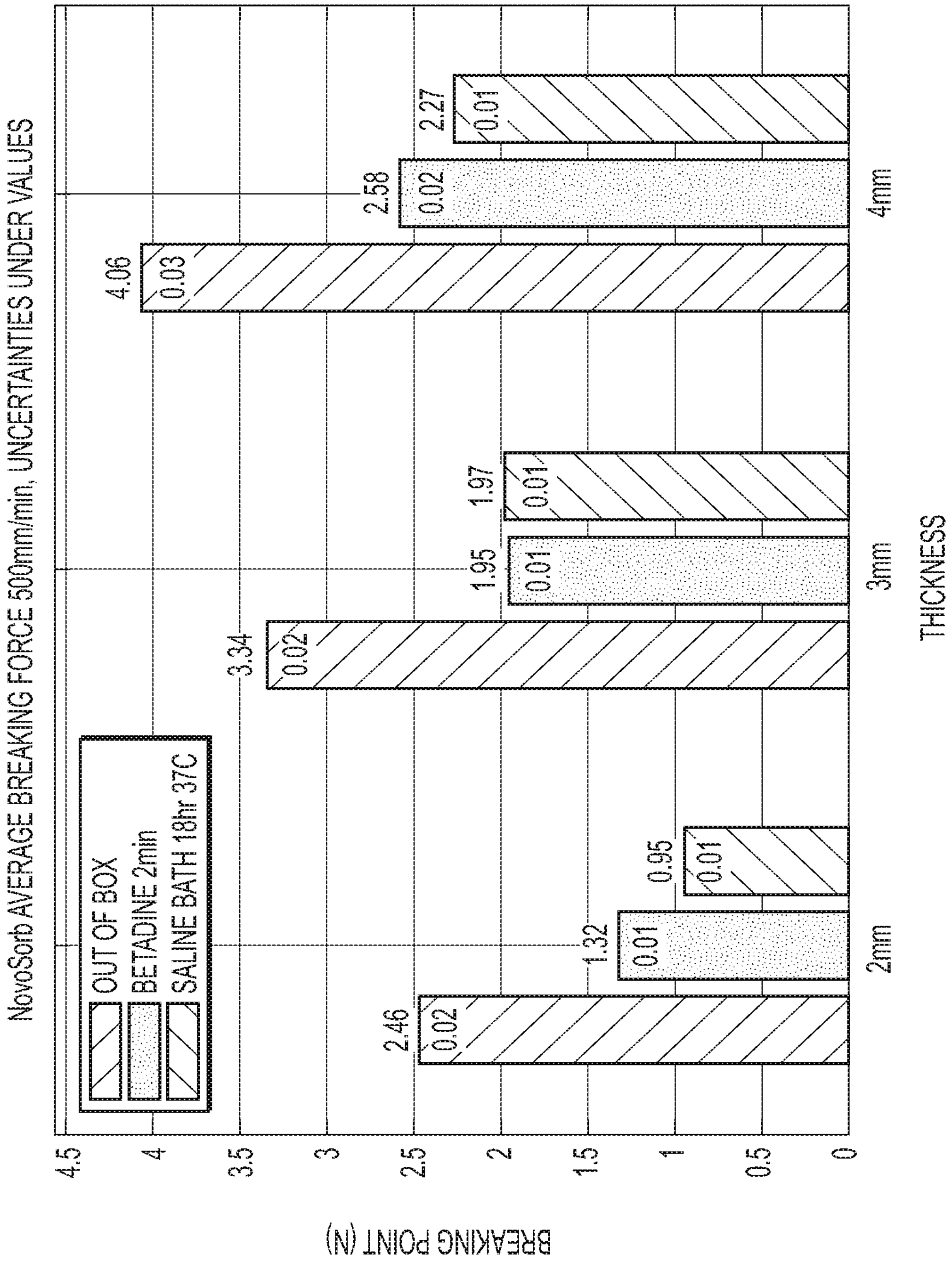
FIG. 10 shows test results described in Example 1.

The strength of polyurethane/urea scaffolding materials was tested under various conditions. In this test, the breaking point of scaffolding materials having thicknesses of 2 mm, 3 mm, and 4 mm was tested at a strain rate of 500 mm/min. The materials were tested under three conditions: (1) an "out of box" condition as a reference where the scaffolding material comes directly from packaging, (2) a "betadine 2 minutes" condition wherein the scaffolding material was soaked in a disinfectant, betadine, and (3) a "saline bath 18 hours 37 C" condition simulating the physiological environment in a human body. Results are shown in FIG. 10, wherein thicker scaffolding corresponded to greater strength. Additionally, the scaffolding had the highest breaking point in the "out of box" condition, second highest breaking point in the "betadine 2 minutes" condition, and lowest breaking point in the "saline bath 18 hours 37 C" condition.

The polyurethane/urea scaffolding materials were also tested in vivo in conjunction with a texturized breast implant to analyze biological response to the scaffolding materials. The in vivo testing was performed in both mice and pig models. The in vivo testing in pigs was conducted on two pigs, with scaffolding materials placed adjacent to a Motiva Breast implant for a period of 72 days, with histology (Massons Trichromes and H&E staining) and SEM imaging later performed on explanted samples. The in vivo testing in mice was conducted on 30 mice organized into two groups of 15 mice each. One group was treated by implanting the scaffolding material alone, and the other group was treated by implanting a tiny breast implant with the same scaffolding material. Each of these groups was evaluated at 3 weeks, 6 weeks, and 12 weeks.

It will be understood that the examples illustrated and described herein are examples and non-limiting as to additional embodiments encompassed herein. The present disclosure is not limited to the exemplary shapes, sizes, and/or materials discussed herein. A person of ordinary skill in the art will recognize that additional shapes, sizes, and/or materials may be used as discussed herein to achieve the same or similar effects or benefits as discussed above. Moreover, the scaffolding may include one or more shapes disclosed herein, or may be any shape known to one skill in the art consistent with the guidance and principles disclosed herein.

We claim:

1. A method of treating a patient, the method comprising:

implanting a scaffolding construct comprising a first biocompatible material into a body of a patient;

wherein the scaffolding construct includes a porous structure and the scaffolding construct is at least partially bioresorbable, the scaffolding construct having an average pore size less than 50 μm; and injecting a second biocompatible material within the porous structure proximate in time to implanting the scaffolding construct into a body of a patient;

wherein injecting the second biocompatible material includes:

embedding the second biocompatible material within one or more pores of the porous structure of the scaffolding construct;

wherein the scaffolding construct defines a cavity that includes an implant, the injected second biocompatible material, or both; and wherein the scaffolding construct facilitates formation of a soft tissue capsule at a site of implantation in the body of the patient.

2. The method of claim 1, wherein the first biocompatible material comprises polyurethane, polyurethane/urea, poly (glycolic acid), poly (lactic acid), poly (lactic-co-glycolic acid), polycaprolactone, agarose, alginate, chitosan, collagen, fibrin, gelatin, hyaluronic acid, gelatin methacryloyl, polyethylene glycol, or a mixture thereof.

3. The method of claim 1, wherein the scaffolding construct has a reabsorption time in the body of the patient ranging from 6 months to about 24 months.

4. The method of claim 1, wherein the cavity includes an implant and the second biocompatible material, the second biocompatible material comprising fat, a natural filler, a synthetic filler, hyaluronic acid, collagen, or a combination thereof.

5. The method of claim 4, wherein the second biocompatible material comprises fat that is autologous to the patient.

6. The method of claim 1, wherein the cavity of the scaffolding construct contains a breast implant.

* * * * *